(12) United States Patent
Wallace et al.

(10) Patent No.: US 6,391,302 B1
(45) Date of Patent: May 21, 2002

(54) METHOD FOR TREATING CANCERS WHICH PRESENT ANTIGEN FB5 WITH HUMANIZED ANTIBODIES

(75) Inventors: Thomas Paul Wallace, Methlick; Francis Carr, Balmedie, both of (GB); Wolfgang J. Rettig; Pilar Garin-Chesa, both of Biberach (DE); Lloyd J. Old, New York, NY (US)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/633,653

(22) Filed: Aug. 7, 2000

Related U.S. Application Data

(62) Division of application No. 09/184,198, filed on Nov. 2, 1998, now Pat. No. 6,217,868, which is a division of application No. 09/013,872, filed on Jan. 27, 1998, now Pat. No. 6,090,930, which is a division of application No. 08/657,012, filed on May 20, 1996, now Pat. No. 5,811,522, which is a continuation of application No. 08/207,778, filed on Mar. 8, 1994, now abandoned.

(51) Int. Cl.[7] .............................................. A61K 39/395
(52) U.S. Cl. ................ 424/181.1; 424/183.1; 424/130.1; 530/388.85; 530/391.3
(58) Field of Search ........................... 424/130.1, 134.1, 424/155.1, 156.1, 178.1, 183.1, 181.1; 530/387.1, 389.3, 388.85, 391.7, 391.3, 388.8

(56) References Cited

FOREIGN PATENT DOCUMENTS

WO    WO 95/24483    *    9/1995

OTHER PUBLICATIONS

Seaver, Genetic Engineering News 14:p 10 and 21, 1994.*
Chatterjee et al., Cancer Immunol. Immunother. 38:75–82, 1994.*
Gura, Science 278:1041–2, 1997.*
Jian, Sci. Amer. 271:58–65, 1994.*

\* cited by examiner

*Primary Examiner*—Sheela Huff
*Assistant Examiner*—Larry R. Helms
(74) *Attorney, Agent, or Firm*—Fulbright & Jaworski LLP

(57) ABSTRACT

The invention provides for the production of several humanized murine antibodies specific for the antigen FB5, which is recognized by the murine antibody FB5. The FB5 antigen is expressed on the luminal surface of vascular endothelial cells of a wide range of malignant tumours. The invention also provides for numerous polynucleotide encoding humanized FB5 specific antibodies, expression vectors for producing humanized FB5 specific antibodies, and host cells for the recombinant production of the humanized antibodies. The invention also provides methods for detecting cancerous cells (in vitro and in vivo) using humanized FB5 specific antibodies. Additionally, the invention provides methods of treating cancer using FB5 specific antibodies.

14 Claims, 10 Drawing Sheets

FIG. 1

```
CAGGTSMARCTGCAGSAGTCWGGACCTGAGCTGGTGAAGCCTGGGGCTTC
----.----+----.----+----.----+----.----+----.----+   50
GTCCASKTYGACGTCSTCAGWCCTGGACTCGACCACTTCGGACCCCGAAG
 q   v  k/q  l   q e/q  s   g   p   e   l   v   k   p   g   a   s

----.----+----.----+----.----+----.----+----.----+
AGTGAAGATGTCCTGCAAGGCTTCTGGATACACATTCACTGACTATGTTA
----.----+----.----+----.----+----.----+----.----+  100
TCACTTCTACAGGACGTTCCGAAGACCTATGTGTAAGTGACTGATACAAT
  v   k   m   s   c   k   a   s   g   y   t   f   t   d   y   v   i

----.----+----.----+----.----+----.----+----.----+
TACACTGGATGAAGCAGAGAAATGGAAAGAGCCTTGAGTGGATTGGATAT
----.----+----.----+----.----+----.----+----.----+  150
ATGTGACCTACTTCGTCTCTTTACCTTTCTCGGAACTCACCTAACCTATA
   h   w   m   k   q   r   n   g   k   s   l   e   w   i   g   y

----.----+----.----+----.----+----.----+----.----+
ATTAATCCTTATGATGATGATACTACCTACAACCAGAAGTTCAAGGGCCA
----.----+----.----+----.----+----.----+----.----+  200
TAATTAGGAATACTACTACTATGATGGATGTTGGTCTTCAAGTTCCCGGT
   i   n   p   y   d   d   d   t   t   y   n   q   k   f   k   g   q

----.----+----.----+----.----+----.----+----.----+
GGCCACATTGACTGTAGTCAAATCCTCCAACACAGCCTACATGCAGCTCA
----.----+----.----+----.----+----.----+----.----+  250
CCGGTGTAACTGACATCAGTTTAGGAGGTTGTGTCGGATGTACGTCGAGT
    a   t   l   t   v   v   k   s   s   n   t   a   y   m   q   l   n

----.----+----.----+----.----+----.----+----.----+
ACAGCCTGACATCTGAGGACTCTGCAGTCTATTACTGTGCAAGAAGGGGG
----.----+----.----+----.----+----.----+----.----+  300
TGTCGGACTGTAGACTCCTGAGACGTCAGATAATGACACGTTCTTCCCCC
    s   l   t   s   e   d   s   a   v   y   y   c   a   r   r   g

----.----+----.----+----.----+----.----+----.----+
AATTCCTATGATGGTTACTTCGACTATTCTATGGACTACTGGGGTCAAGG
----.----+----.----+----.----+----.----+----.----+  350
TTAAGGATACTACCAATGAAGCTGATAAGATACCTGATGACCCCAGTTCC
   n   s   y   d   g   y   f   d   y   s   m   d   y   w   g   q   g

----.----+----.----+----.----+----.----+----.----+
AACCTCAGTCACCGTCTCCTCA
----.----+----.----+--   372
TTGGAGTCAGTGGCAGAGGAGT
   t   s   v   t   v   s   s
----.----+----.----+--
```

FIG. 2

```
GACATTGTGATGACCCAGTCTCAAAAATTCATGTCCACATCAGTAGGAGA
----.----+----.----+----.----+----.----+----.----+   50
CTGTAACACTACTGGGTCAGAGTTTTTAAGTACAGGTGTAGTCATCCTCT
 d  i  v  m  t  q  s  q  k  f  m  s  t  s  v  g  d

----.----+----.----+----.----+----.----+----.----+

CAGGGTCAACATCACCTGCAGGGCCAGTCAGAATGTGGGTACTGCTGTAG
----.----+----.----+----.----+----.----+----.----+   100
GTCCCAGTTGTAGTGGACGTCCCGGTCAGTCTTACACCCATGACGACATC
 r  v  n  i  t  c  r  a  s  q  n  v  g  t  a  v  a

----.----+----.----+----.----+----.----+----.----+

CCTGGTATCAACAGAAACCAGGACAATCTCCTAAATTACTGATTTACTCG
----.----+----.----+----.----+----.----+----.----+   150
GGACCATAGTTGTCTTTGGTCCTGTTAGAGGATTTAATGACTAAATGAGC
 w  y  q  q  k  p  g  q  s  p  k  l  l  i  y  s

----.----+----.----+----.----+----.----+----.----+

GCATCGAATCGGTACACTGGAGTCCCTGATCGCTTCACAGGCAGTGGATC
----.----+----.----+----.----+----.----+----.----+   200
CGTAGCTTAGCCATGTGACCTCAGGGACTAGCGAAGTGTCCGTCACCTAG
 a  s  n  r  y  t  g  v  p  d  r  f  t  g  s  g  s

----.----+----.----+----.----+----.----+----.----+

TGGGACAGATTTCACTCTCACCATCAGCAATATGCAGTCTGAAGACCTGG
----.----+----.----+----.----+----.----+----.----+   250
ACCCTGTCTAAAGTGAGAGTGGTAGTCGTTATACGTCAGACTTCTGGACC
 g  t  d  f  t  l  t  i  s  n  m  q  s  e  d  l  a

----.----+----.----+----.----+----.----+----.----+

CAGATTATTTCTGCCAGCAATATACCAACTATCCATGTACACGTTTGGA
----.----+----.----+----.----+----.----+----.----+   300
GTCTAATAAAGACGGTCGTTATATGGTTGATAGGGTACATGTGCAAACCT
 d  y  f  c  q  q  y  t  n  y  p  m  y  t  f  g

----.----+----.----+----.----+----.----+----.----+

GGGGGGACCAAGCTGGAAATAAAA
----.----+----.----+----    324
CCCCCCTGGTTCGACCTTTATTTT
 g  g  t  k  l  e  i  k

----.----+----.----+----
```

METHOD FOR TREATING CANCERS WHICH PRESENT ANTIGEN FB5 WITH HUMANIZED ANTIBODIES

RELATED APPLICATIONS

This application is a divisional of Ser. No. 09/184,198, filed Nov. 2, 1998, now U.S. Pat. No. 6,217,868, which is a divisional of Ser. No. 09/013,872, filed on Jan. 27, 1998, now U.S. Pat. No. 6,090,930, which is a divisional of Ser. No. 08/657,012, filed on May 20, 1996, now U.S. Pat. No. 5,811,522 which is a continuation of Ser. No. 08/207,778, filed on Mar. 8, 1994, now abandoned.

FIELD OF THE INVENTION

The present invention is related to the field of molecular biology, and more particularly to humanized antibodies.

BACKGROUND

The present invention relates to the generation, by recombinant DNA methods, of novel recombinant immunoglobulins specific for the human FB5 (endosialin) cancer antigen. The invention also discloses methods for the production of these recombinant antibodies, for the diagnosis and treatment of certain human cancers.

Transformation of a normal cell to a malignant cell is often accompanied by a change in the expression of cell surface antigens. These different phenotypes can be detected using monoclonal antibodies specific for such antigens. In this way, different cancer cells can be detected and characterized (Lloyd, K. O. (1983) "Human Tumour Antigens: Detection and Characterization with Monoclonal Antibodies" in R. B. Herberman, ed., Basic and Clinical Tumour Immunology, pp 159–214, Martinus Nijhoff, Boston). These cell surface antigens are appropriate targets for tumour immunotherapy and diagnosis.

Of particular value for the diagnosis and therapy of a broad range of cancers would be the identification of an antigen associated with a broad range of cancers. Tumour stromas are potential sites for the location of such antigens. One such antigen (F19) is expressed on the surface of reactive stromal fibroblasts associated with >90% of epithelial cancers (Garin-Chesa, P. et al. (1990) Proc. Natl Acad. Sci. 87, 7235–7239; Rettig, W. J. et al. (1988) Proc. Natl Acad. Sci. 85, 3110–3114). In clinical trials, a monoclonal antibody specific for the F19 antigen accumulated at tumour sites successfully locating hepatic metastases from colorectal carcinomas (Welt, S. et al. (1992) Proc. Am. Assoc. Cancer Res. 33, 319). This illustrates the diagnostic potential of monoclonal antibodies specific for tumour stromal antigens. Another tumour stromal antigen (FB5 or 'endosialin') has been identified and partially characterized (Rettig, W. J. et al. (1992) Proc. Natl Acad. Sci. 89, 10832–10836). A murine monoclonal antibody (mAbFB5) has been raised against the FB5 antigen. This antibody has been used to show that the FB5 antigen is expressed on the luminal surface of vascular endothelial cells of a wide range of malignant tumours. Specifically, in immunohistochemical analyses of vascular endothelial cells of human tumours, FB5 expression was found in 26 of 36 carcinomas, 18 of 25 neuroectodermal tumours and 41 of 61 sarcomas. In contrast, it could not be detected in any of a wide range of normal adult tissues including tissues of the following organ systems: breast, cardiovascular, connective tissues, digestive tract, endocrine, haematopoietic, lymphoid, reproductive, skin and urinary. Similary, FB5 was not expressed in cultured human malignant cells (excepting a subset of sarcomas), and stromal fibroblasts of only a small proportion of epithelial cancers exhibited FB5 expression.

The specificity of the FB5 murine antibody makes it a powerful tool for the detection of human cancers in vitro. For a number of reasons the location of the FB5 antigen on the luminal surface of tumour vascular endothelial cells makes the antigen an ideal target for tumour immunotherapy and diagnosis in vivo. Firstly, a wide range of cancer types may be diagnosed and treated by the FB5 antibody (or antibody conjugate). Secondly, the endothelial cell surface is readily accessible to antibodies that are circulating in the blood stream. Thirdly, antibody-targeted destruction of tumour blood vessels could lead to widespread necrosis in solid tumours. Finally, on binding to FB5—expressing cells the mAbFB5 is rapidly internalized raising the possibility that the antibody could be used for the specific delivery of cytoxic agents for the destruction of tumour blood vessels. However, the in vivo use of murine antibodies as agents for the diagnosis and treatment of human diseases in severely curtailed by a number of factors. Specifically, the human body recognises murine antibodies as foreign. This recognition of the murine antibodies can elicit a human anti-mouse antibody (HAMA) response (Schroff, R. et al. (1985) Cancer Res. 45, 879–885) which results in rapid clearance of the antibody from the circulation. Furthermore, the Fc portion of a murine antibody is not as efficacious as the human Fc at stimulating human complement or cell-mediated cytotoxicity. For the in vivo use of murine antibodies in diagnosis and therapy, these problems must be circumvented.

EP120694 (Celltech) and EP125023 (Genentech) disclose the development of 'chimaeric' antibodies using recombinant DNA methods. Such antibodies comprise the variable regions from one species (eg mouse) and the constant regions from another species (eg human).

Such chimaeric antibodies would have the advantage that they retain the specificity of the murine antibody but can also stimulate human Fc dependent complement fixation and cell-mediated cytotoxicity. However, the murine variable regions can still elicit a HAMA response (Bruggemann, M. et al. (1989) J. Exp. Med. 170, 2153–2157) thereby limiting the value of chimaeric antibodies as diagnostic and therapeutic agents.

British Patent Application Number CR2199929A (Winter) discloses a process whereby recombinant antibodies can be generated by substitution of only the variable region CDRs of one antibody with those from another. Typically, this 'CDR-grafting' technology has been applied to the generation of recombinant, pharmaceutical antibodies consisting of murine CDRs, human variable region frameworks and human constant regions (eg Riechmann, L. et al, (1988) Nature, 332, 323–327). Such 'reshaped' or 'humanized' antibodies have less murine content than chimaeric antibodies and retain the human constant regions necessary for the stimulation of human Fc dependent effector functions. In consequence, CDR grafted antibodies are less likely than chimaeric antibodies to evoke a HAMA response when administered to humans, their half-life in circulation should approach that of natural human antibodies and their diagnostic and therapeutic value is enhanced.

In practice, for the generation of efficacious humanized antibodies retaining the specificity of the original murine antibody, it is not usually sufficient simply to substitute CDRs. In addition there is a requirement for the inclusion of a small number of critical murine antibody residues in the human variable region. The identity of these residues depends on the structure of both the original murine antibody and the acceptor human antibody. British Patent Application Number 9019812.8 discloses a method for identifying a minimal number of substitutions of foreign residues sufficient to promote efficacious antigen binding.

The present invention provides novel, humanized monoclonal antibodies specific for the human FB5 cancer antigen. This has been achieved by the conversion of the murine FB5 monoclonal antibody to humanized antibodies by utilising CDR-grafting technologies. The invention also provides methods for the production of these humanized antibodies to be used in the diagnosis and treatment of certain human cancers. Prior to the work of the inventors, it was not known that FB5 or any other non-human antibody specific for the the FB5 antigen could be humanized so as to retain useful binding specificity.

BRIEF DESCRIPTION OF THE FIGURES

FIG. 1 Shows the DNA sequence and corresponding amino acid sequence of the murine FB5 heavy chain variable region (VH). The CDRs are boxed. Underlined nucleotides and amino acid residues are derived from the oligonucleotide primers used. A backslash is used to indicate the result obtained by the use of consensus primers.

FIG. 2 Shows the DNA sequence and corresponding amino acid sequence of the murine FB5 light chain variable region (VK). The CDRs are boxed. Underlined nucleotides and amino acid residues are derived from the oligonucleotide primers used.

SUMMARY OF THE INVENTION

Figure 3:
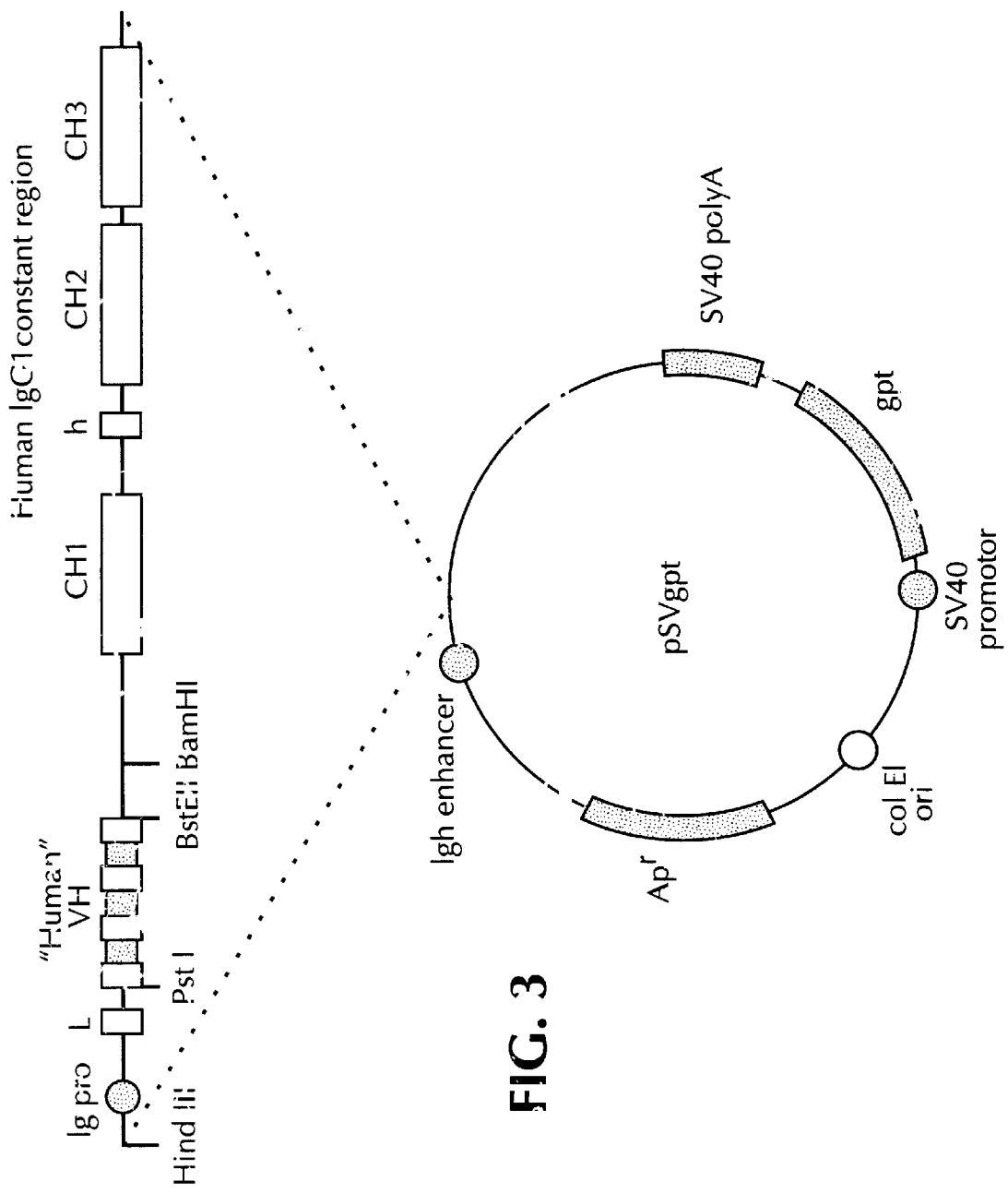
FIG. 3 Shows the vector psvgpt for the expression of chimaeric or humanized heavy chains in mammalian cells.

One aspect of the invention is to provide humanized antibodies specific for the FB5 antigen.

Another aspect of the invention is to provide polynucleotides encoding humanized antibodies specific for the FB5 antigens. Various expression vectors comprising polynucleotides encoding humanized FB5 antibodies joined to promoter sequences are also provided. Similarly, another aspect of the invention is host cells transformed with expression vectors for the expression of humanized FB5 specific antibodies.

Another aspect of the invention is to provide humanized anti-FB5 antibodies that are labeled with a detectable label or a therapeutic label.

Another aspect of the invention is to provide methods for treating and/or diagnosing cancer by administering a composition comprising a humanized FB5 specific antibody. One method of detecting cancer cells involves the steps of administering a labeled antibody (detectable label) to a patient and subsequently detecting where in the body the labeled antibody has bound.

DETAILED DESCRIPTION OF THE SPECIFIC EMBODIMENTS

As used herein, the term "humanized" antibody refers to a molecule that has its CDRs (complementarily determining regions) derived from a non-human species immunoglobulin and the remainder of the antibody molecule derived mainly from a human immunoglobulin. The term "antibody" as used herein, unless indicated otherwise, is used broadly to refer to both antibody molecules and a variety of antibody derived molecules. Such antibody derived molecules comprise at least one variable region (either a heavy chain of light chain variable region) and include molecules such as Fab fragments, Fab' fragments, F(ab')$_2$ fragments, Fd fragments, Fab' fragments, Fd fragments, Fabc fragments, Sc antibodies (single chain antibodies), diabodies, individual antibody light chains, individual antibody heavy chains, chimeric fusions between antibody chains and other molecules, and the like.

The term "conventional molecular biology methods" refers to techniques for manipulating polynucleotides that are well known to the person of ordinary skill in the art of molecular biology. Examples of such well known techniques can be found in *Molecular Cloning: A Laboratory Manual 2nd Edition,* Sambrook et al, Cold Spring Harbor, N.Y. (1989). Examples of conventional molecular biology techniques include, but are not limited to, in vitro ligation, restriction endonuclease digestion, PCR, cellular transformation, hybridization, electrophoresis, DNA sequencing, cell culture, and the like.

The term "variable region" as used herein in reference to immunoglobulin molecules has the ordinary meaning given to the term by the person of ordinary skill in the act of immunology. Both antibody heavy chains and antibody light chains may be divided into a "variable region" and a "constant region". The point of division between a variable region and a heavy region may readily be determined by the person of ordinary skill in the art by reference to standard texts describing antibody structure, e.g., Kabat et al "Sequences of Proteins of Immunological Interest: 5th Edition" U.S. Department of Health and Human Services, U.S. Government Printing Office (1991).

The present invention provides humanized antibody molecules specific for FB5 antigen in which at least parts of the CDRs of the heavy and/or light chain variable regions of a human antibody (the receptor antibody) have been substituted by analogous parts of CDRs of a murine monoclonal antibody and the humanized antibody can specifically bind to the same as the FB5 antibody. In a preferred embodiment of the subject invention, the CDR regions of the humanized FB5 specific antibody are derived from the murine antibody FB5. Some of the the humanized antibodies described herein contain some alterations of the acceptor antibody, i.e., human, heavy and/or light chain variable domain framework regions that are necessary for retaining binding specificity of the donor monoclonal antibody. In other words, the framework region of some embodiments the humanized antibodies described herein does not necessarily consist of the precise amino acid sequence of the framework region of a natural occurring human antibody variable region, but contains various substitutions that improve the binding properties of a humanized antibody region that is specific for the same target as the murine FB5 specific antibody. A minimal number of substitutions are made to the framework region in order to avoid large-scale introductions of non-human framework residues and to ensure minimal immunogenicity of the humanized antibody in humans. The donor monoclonal antibody of the present invention is the FB5 murine antibody, which is specific for the human FB5 cancer antigen.

The humanized antibodies of the present invention include complete antibody molecules having full length heavy and light chains, or any fragment thereof, such as the Fab or (Fab')$_2$ fragments, a heavy chain and light chain dimer, or any minimal fragment thereof such as a Fv, an SCA (single chain antibody), and the like, specific for the FB5 antigen molecule.

In addition to providing for humanized FB5 specific antibodies, the subject invention provides for polynucleotides encoding humanized FB5 specific antibodies. The subject polynucleotides may have a wide variety of sequences because of the degeneracy of the genetic code. A person of ordinary skill in the art may readily change a given polynucleotide sequence encoding a humanized FB5 specific antibody into a different polynucleotide encoding the same humanized FB5 specific antibody embodiment. The polynucleotide sequence encoding the antibody may be varied to take into account factors affecting expression such as codon frequency, RNA secondary structure, and the like.

The humanized antibodies of the subject invention may be produced by a variety of methods useful for the production of polypeptides, e.g. in vitro synthesis, recombinant DNA production, and the like. Preferably, the humanized antibodies are produced by recombinant DNA technology.

The humanized FB5 specific antibodies of the invention may be produced using recombinant immunoglobulin expression technology. The recombinant production of immunoglobulin molecules, including humanized antibodies are described in U.S. Pat. No. 4,816,397 (Boss et al), U.S. Pat. No. 4,816,567 (Cabilly et al) U.K. patent GB 2,188,638 (Winter et al), and U.K. patent GB 2,209,757. Techniques for the recombinant expression of immunoglobulins, including humanized immunoglobulins, can also be found, among other places in Goeddel et al, *Gene Expression Technology Methods in Enzymology Vol.* 185 Academic Press (1991), and Borreback, *Antibody Engineering,* W. H. Freeman (1992). Additional information concerning the generation, design and expression of recombinant antibodies can be found in Mayforth, *Designing Antibodies,* Academic Press, San Diego (1993).

The recombinant humanized anti-FB5 antibodies of the invention may be produced by the following process or other recombinant protein expression methods:

a. Constructing, by conventional molecular biology methods, an expression vector comprising an operon that encodes an antibody heavy chain in which the CDRs and a minimal portion of the variable region framework that are required to retain donor antibody binding specificity are derived from a non-human immunoglobulin, such as the murine FB5 monoclonal antibody, and the remainder of the antibody is derived from a human immunoglobulin, thereby producing a vector for the expression of a humanized antibody heavy chain.

b. constructing, by conventional molecular biology methods, an expression vector comprising an operon that encodes an antibody light chain in which the CDRs and a minimal portion of the variable region framework that are required to retain donor antibody binding specificity are derived from a non-human immunoglobulin, such as the murine FB5 monoclonal antibody, and the remainder of the antibody is derived from a human immunoglobulin, thereby producing a vector for the expression of humanized antibody light chain.

c. Transferring the expression vectors to a host cell by conventional molecular biology methods to produce a transfected host cell for the expression of humanized anti-FB5 antibodies.

d. Culturing the transfected cell by conventional cell culture techniques so as to produce humanized anti-FB5 antibodies.

Host cells may be cotransfected with two expression vectors of the invention, the first vector containing an operon encoding a heavy chain derived polypeptide and the second containing an operon encoding a light chain derived polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both.

The host cell used to express the recombinant antibody of the invention may be either a bacterial cell such as *Escherichia coli,* or preferably a eukaryotic cell. Preferably a mammalian cell such as a chinese hamster ovary cell, may be used. The choice of expression vector is dependent upon the choice of host cell, and may be selected so as to have the desired expression and regulatory characteristics in the selected host cell.

The general methods for construction of the vector of the invention, transfection of cells to produce the host cell of the invention, culture of cells to produce the antibody of the invention are all conventional molecular biology methods. Likewise, once produced, the recombinant antibodies of the invention may be purified by standard procedures of the art, including cross-flow filtration, ammonium sulphate precipitation, affinity column chromatography, gel electrophoresis and the like.

The humanized FB5 specific antibodies of the present invention may be used in conjunction with, or attached to other antibodies (or parts thereof) such as human or humanized monoclonal antibodies. These other antibodies may be reactive with other markers (epitopes) characteristic for the disease against which the antibodies of the invention are directed or may have different specificities chosen, for example, to recruit molecules or cells of the human immune system to the diseased cells. The antibodies of the invention (or parts thereof) may be administered with such antibodies (or parts thereof) as separately administered compositions or as a single composition with the two agents linked by conventional chemical or by molecular biological methods. Additionally the diagnostic and therapeutic value of the antibodies of the invention may be augmented by labelling the humanized antibodies with labels that produce a detectable signal (either in vitro or in vivo) or with a label having a therapeutic property. Some labels, e.g. radionucleotides may produce a detectable signal and have a therapeutic property. Examples of radionuclide labels include $^{125}$I, $^{131}$I, $^{14}$C. Examples of other detectable labels include a fluorescent chromophore such as fluorescein, phycobiliprotein or tetraethyl rhodamine for fluorescence microscopy, an enzyme which produces a fluorescent or colored product for detection by fluorescence, absorbance, visible color or agglutination, which produces an electron dense product for demonstration by electron microscopy; or an electron dense molecule such as ferritin, peroxidase or gold beads for direct or indirect electron microscopic visualization. Labels having therapeutic properties include drugs for the treatment of cancer, such as methotrexate and the like.

The subject invention also provides for a variety of methods for treating and/or detecting cancer cells. These methods involve the administration to of humanized FB5 specific antibodies, either labelled or unlabelled, to a patient.

One method of detecting cancer cells in a human involves the step of administering a labeled humanized FB5 specific antibody (labelled with a detectable label) to a human and subsequently detecting bound labeled antibody by the presence of the label.

The recombinant antibodies of this invention may also be used for the selection and/or isolation of human monoclonal antibodies, and the design and synthesis of peptide or non-peptide compounds (mimetics) which would be useful for the same diagnostic and therapeutic applications as the antibodies (e.g. Saragovi et al., (1991) *Science* 253:792–795).

When the humanized FB5 specific antibodies of the invention are used in vitro, the antibodies are typically administered in a composition comprising a pharmaceutical carrier. A pharmaceutical carrier can be any compatible, non-toxic substance suitable for delivery of the monoclonal antibodies to the patient, Sterile water, alcohol, fats, waxes, and inert solids may be included in the carrier. Pharmaceutically accepted adjuvants (buffering agents, dispersing agent) may also be incorporated into the pharmaceutical composition.

The humanized antibodies compositions of the invention may be administered to a patient in a variety of ways. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, *Remington's Pharmaceutical Science*, 15th Ed., Mack Publishing Company, Easton, Pa. (1980), which is incorporated herein by reference.

The subject invention provide numerous humanized antibodies specific for the FB5 antigen based on the discovery that the CDR regions of the murine monoclonal antibody could be spliced into a human acceptor framework so as to produce a humanized recombinant antibody specific for the FD5 antigen. Preferred humanized FB5 specific antibodies contain additional change in the framework region (or in other regions) to increasing binding for FB5 antigen. Particularly preferred embodiments of the invention are the exemplified humanized antibody molecules that have superior binding properties for FB5.

The following examples are offered by way of illustration of the invention, and should not be interpreted as a limitation of the invention.

EXAMPLES

In the following examples all necessary restriction and modification enzymes, plasmids and other reagents and materials were obtained from commercial sources unless otherwise indicated.

Unless otherwise indicated, all general recombinant DNA methodology was performed as described in "Molecular Cloning, A Laboratory Manual" (1989) Eds J. Sambrook et al., published by Cold Spring Harbor Laboratory Press, Cold Spring Harbor, N.Y.

In the following examples these abbreviations may be employed:

| | |
|---|---|
| dCTP | deoxycytidine triphosphate |
| dATP | deoxyadenosine triphosphate |
| dGTP | deoxyguanosine triphosphate |
| dTTP | deoxythymidine triphosphate |
| DTT | dithiothreitol |
| C | cytosine |
| A | adenine |
| G | guanine |
| T | thymine |
| PBS | phosphate buffered saline |
| PBSB | phosphate buffered saline containing 0.5% (w/v) bovine serum albumin |
| PBST | phosphate buffered saline containing 0.05% (v/v) Tween –20 |

Example 1

Production of Humanized Antibodies Specific for the FB5 Antigen

The source of the donor CDRs used to prepare these recombinant antibodies was a murine monoclonal antibody, mAbFB5, which is specific for the FB5 antigen of certain human cancers (Rettig, W. J. et al. (1992) Proc. Natl Acad. Sci. 89, 10832–10836). The FB5 monoclonal antibody was produced by immunisation of (BALB/c×A) $F_1$ mice with human fibroblasts and subsequent production and screening of hybridoma cells. Cytoplasmic RNA was prepared from the mAb FB5 hybridoma cell line by the method of Favoloro, J. et al., (1980), Methods in Enzymology, 65, 718–749). cDNA was synthesised using Ig variable region primers as follows: for the Ig heavy chain variable region (VH), the primer CG2aFOR (5' GGAAGCTTAGAC-CGATGGGGCTGTTGTT TTG 3') (SEQ ID NO:1); for the light chain variable region (VK), the primer CK2FOR (5' GGAAGCTTGAAGATGGATACAGTTGGTGCAGC 3') (SEQ ID NO:2). cDNA synthesis reactions consisted of 4 µg RNA, 25 pmol CG2aFOR or CK2FOR, 250 µM each of dATP, dCTP, dGTP and dTTP, 100 mM TrisHCl pH8.3, 140 mM KCl, 10 mM DTT, 10 mM $MgCl_2$ and 31.5 units of RNase inhibitor (Pharmacia, Milton Keynes, U.K.) in a total volume of 50 µl. Samples were heated to 70° C. for 10 minutes (min) then slowly cooled to 42° C. over a period of 30 min. 100 units of Moloney Murine Leukaemia virus (M-MLV) reverse transcriptase (Life Technologies Ltd, Paisley, U.K.) was added and incubation at 42° C. continued for 1 hour.

VH and VK cDNAs were then amplified using the polymerase chain reaction (PCR) as described by Saiki, R. K. et al., (1988), Science, 239, 487–491. The primers used were:

CG2aFOR (5' GGAAGCTTAGACCGATGGGGCTGT-
TGTT TTG 3') (SEQ ID NO:1)

CK2FOR (5' GGAAGCTTGAAGATGGATACAGTTG-
GTGCAGC 3') (SEQ ID NO:2)

VH1BACK (5' AGGTSMARCTGCAGSAGTCWGG 3') (SEQ ID NO:3)

SK2BACK (5' ACTAGTCGACATGGRCT-THMAGRTGSAG 3') (SEQ ID NO:4)

where M=C or A, H=not G, R=A or G, S=C or G, and W=A or T. Such primers and their use in the PCR amplification of mouse Ig DNA are described by Orlandi, R. et al., (1989), Proc. Natl Acad. Sci. USA, 86, 3833–3837. For PCR amplification of VH, 5 µl RNA/cDNA hybrid was mixed with 25 pmol CG2aFOR and VH1BACK primers. For PCR amplification of VK, 5 µl RNA/cDNA hybrid was mixed with 25 pmol CK2FOR and SK2BACK primers. To these mixtures was added 200 µM each of dATP, dCTP, dGTP and dTTP, 67 mM TrisHCl pH8.8, 17 mM $(NH_4)_2SO_4$, 10 mM $MgCl_2$, 0.02%(w/v) gelatin and 2.5 units of AmpliTaq DNA polymerase (Perkin Elmer Ltd, Beaconsfield, U.K.) in a total volume of 50 µl. These were then subjected to 25 thermal cycles of PCR at 94° C., 30 s; 50° C., 40 s; 72° C., 30 s; ending with 5 min at 72° C. For cloning and sequencing, amplified DNA was purified by electrophoresis in a low melting point agarose gel and by Elutip-d column chromatography (Schleicher and Schuell, Dussel, Germany). Amplified VH DNA was cut with HindIII and PstI and cloned into M13mp18 or M13mp19 cut with HindIII and PstI (Life Technologies Ltd, Paisley, U.K.). Amplified VK DNA was cut with HindIII and SalI and cloned into HindIII and SalI cut M13mp18 or M13mp19 (Life Technologies Ltd, Paisley, U.K,).

The resulting clones were sequenced by the dideoxy method (Sanger, F. et al., (1977), Proc. Natl Acad. Sci. USA, 74, 5463–5467) using Sequenase (United States Biochemical, Cleveland, Ohio, USA). The DNA and protein sequences of the FB5 VH and VK domains are shown in FIGS. 1 and 2. The location of the CDRs was determined with reference to Kabat, E. A. et al. (1987) "Sequences of Protein of Immunological Interest", US Department of Health and Human Services, US Government Printing Office, and utilising computer assisted alignment with other VH and VK sequences.

The transfer of the murine CDRs to human frameworks was achieved by oligonucleotide site-directed mutagenesis, based on the method of Nakamye, K. and Eckstein, F. (1986) Nucleic Acids Res. 14, 9679–9698. The human framework regions chosen to receive the transplanted CDRs were NEWM and REI for the heavy and light chains respectively. The structures of these proteins have been solved crystallographically. The templates for mutagenesis were human framework region genes containing irrelevant CDRs and consisted of synthetic DNAs cloned into M13 phage (Riechmann, L. et al. (1988) Nature, 332, 323–327). The oligonucleotides used were:

```
NEWM VH

VHCDR1 5'
    CGTCCAGGTGGCTGTCTCACCCAGTGTATAACATAGTCAGTGAA
    GG TGTAGCCAGACGCGGTGCAGGTCAGGCTC 3'
    (SEQ ID NO: 5)
VHCDR2 5'TTGTCACTCTGCCCTTGAACTTCTGGTTGTAGGTAGTATCAT
    CATCATAAGGATTAATATATCCAATCCACTCAAG 3'
    (SEQ ID NO:6)
VHCDR3 5'CCTGAGGAGACGGTGACGAGACTCCCTTGGCCCCAGTAGTCC
    ATAGAGTAGTCAAAGTAACCATCATAGGAATTCCCCCTTCTTGC
    ACAATAATAG 3'
    (SEQ ID NO:7)
```

```
REI VK

VKCDR1 5'GGAGCCTTACCTGGGGTCTGCTGGTACCAGGCTACAGCAGTA
    CCCACATTCTGGCTGGCTCTACAGGTG 3'
    (SEQ ID NO:8)
VKCDR2 5'
    CTGCTTGGCACACCAGTGTACCGATTCGATGCCGAGTAGATCAG
    CAGC 3'
    (SEQ ID NO:9)
VKCDR3 5'CTACTCACGTTTGATTTGCACCTTGGTCCCTTGGCCGAACGT
    GTACATGGGATAGTTGGTATATTGCTGGCAGTAGTAGGTGG 3'
    (SEQ ID NO:10)
```

A number of additional, murine residues were introduced into the variable region frameworks by using a separate oligonucleotide or by extension of the CDR primers. Specifically:

| | | |
|---|---|---|
| NEWM V(24) | changed to A | (NEWM VHCDR1 oligonucleotide) |
| NEWM S(27) | changed to Y | (NEWM VHCDR1 oligonucleotide) |
| NEWM S(30) | changed to T | (NEWM VHCDR1 oligonucleotide) |

NEWM K(75), QFS(77–79), A(85) to S,TAY,E (olignucleotide: 5' CGCGGTGTCCTCGGCTGTCACGCTGCTGAGTCTCAGGTAGGCTGTGTTG GAGCTGGTGTCTACC 3') (SEQ ID NO:11)

These residues that have been changed are believed to be important for retaining original antigen specificity. Although the invention is not dependent upon any particular explanation for the results obtained by making the additional residue changes, some possible explanations for their significance are as follows:

The change of residues NEWM V(24) to the smaller A facilitates the accommodation of the heterlogous CDR1 loop. The NEWM S(27) to Y change was made because S(27) is an unusual residue in subgroup II human heavy chains (Riechmann et al. (1988) Nature 332, 323–327). Amino acids VH(27–30), are residues of the 'vernier zones' as defined by Foote and Winter (Foote, J. and Winter G. (1992) J. Mol. Biol. 224, 487–499. These zones are important for adjusting CDR structures to promote antigen binding. This explanation accounts for the changes NEWM S(27) to Y and NEWM S(30) to T.

For site directed mutagenesis the VH and VK oligonucleotides encoding the murine CDRs and NEWM K, QFS, A change were phosphorylated with T4 Kinase (Life Technologies Ltd, Paisley, U.K.). A 25 fold molar excess of each of the three VH (plus NEWM K, QFS, A primer) or VK primers were added to 0.5 µg of appropriate VH or VK single stranded template DNA in M13 (NEWM VH:M13VHPCR1; REI:M13VKPCR2) in 40 mM Tris HCl pH7.5, 20 mM $MgCl_2$, 50 mM NaCl and annealed by heating to 90° C. for a few minutes and slowly cooling to 37° C. The annealed DNA was extended with 2.5 units of T7 DNA polymerase (cloned, United Staten Biochemical, Cleveland, Ohio, USA) in a reaction mixture containing 0.5 units of T4 DNA ligase (Life Technologies Ltd, Paisley, U.K.), 0.25 mM of each of dATP, dGTP, dTTP, and dCTP (Pharmacia, Milton Keynes, U.K.), 40 mM Tris HCl pH7.5, 20 mM $MgCl_2$, 50 mM NaCl, 6.5 mM DTT and 1 mM ATP in a total volume of 30 µl. The mixture was incubated at room temperature for 1 h. A 1 µl aliquot of this extension/ligation mixture was then used in an asymmetric PCR for the specific amplification of the newly synthesized strand. The reaction contained 1 µl extension/ligation mixture, 250 µM of each of dATP, dGTP, dTTP and dCTP, 67 mM Tris HCl pH8.8, 17 mM $(NH_4)_2SO_4$, 10 mM $MgCl_2$, 0.02% (w/v) gelatin, 2.5 Units of AmpliTaq DNA polymerase and 25 pmol of appropriate oligonucleotide primer (5' AACAGC-TATGACCATG 3' (SEQ ID NO:12) for NEWM VH; 5' CTCTCTCAGGGCCAGGCGGTGA 3' (SEQ ID NO:13) for REI VK) in a total volume of 50 µl. The reaction mixtures were subjected to 30 thermal cycles of PCR at 94° C., 30 s; 55° C., 30 s; 72° C., 1 min ending with 72° C, 5 min. The newly synthesized strand was then amplified by adding 20 pmol of appropriate oligonucleotide primer (5' GTAAAACGACGGCCAGT 3' (SEQ ID NO:14) for NEWM VH and 5' GCGGGCCTCTTCGCTATTACGC 3' (SEQ ID NO:15) for REI VK) and adjusting the reaction mixture to include a further 5 nmols of each of dATP, dGTP, dTTP and dCTP and 2.5 Units of AmpliTaq. The reactions were subjected to a further 20 PCR cycles as above. The amplified VH and VK DNAs were purified from 1.5% w/v low melting point agarose gels by elutip-d column chromatography. Purified DNA was digested with HindIII and BamHI plus RsaI (for VHs) or BstXI (for VKs) (all reaction enzymes from Life Technologies Ltd, Paisley, U.K.). There is an RsaI site in the parental VHPCR1 and a BstXI site in the parental VKPCR2 but these sites are deleted during mutagenesis. These digestions therefore select for newly synthesized DNA. The HindIII/BamHI digested VH and VK DNAs were ligated into HindIII/BamHI cut M13mp18 or M13mp19 (both from Pharmacia, Milton Keynes, U.K.) and transformed into competant *E. coli* TG1 (Amersham International plc, Amersham, U.K.). Single stranded DNA was prepared from individual 'plaques' and sequenced by the dideoxy method using Sequenase (United States Biochemical, Cleveland, Ohio, USA) according to Manufacturer's instructions. Triple CDR mutants were identified in this way and selected for construction of VH and VK expression vectors.

Figure 4:
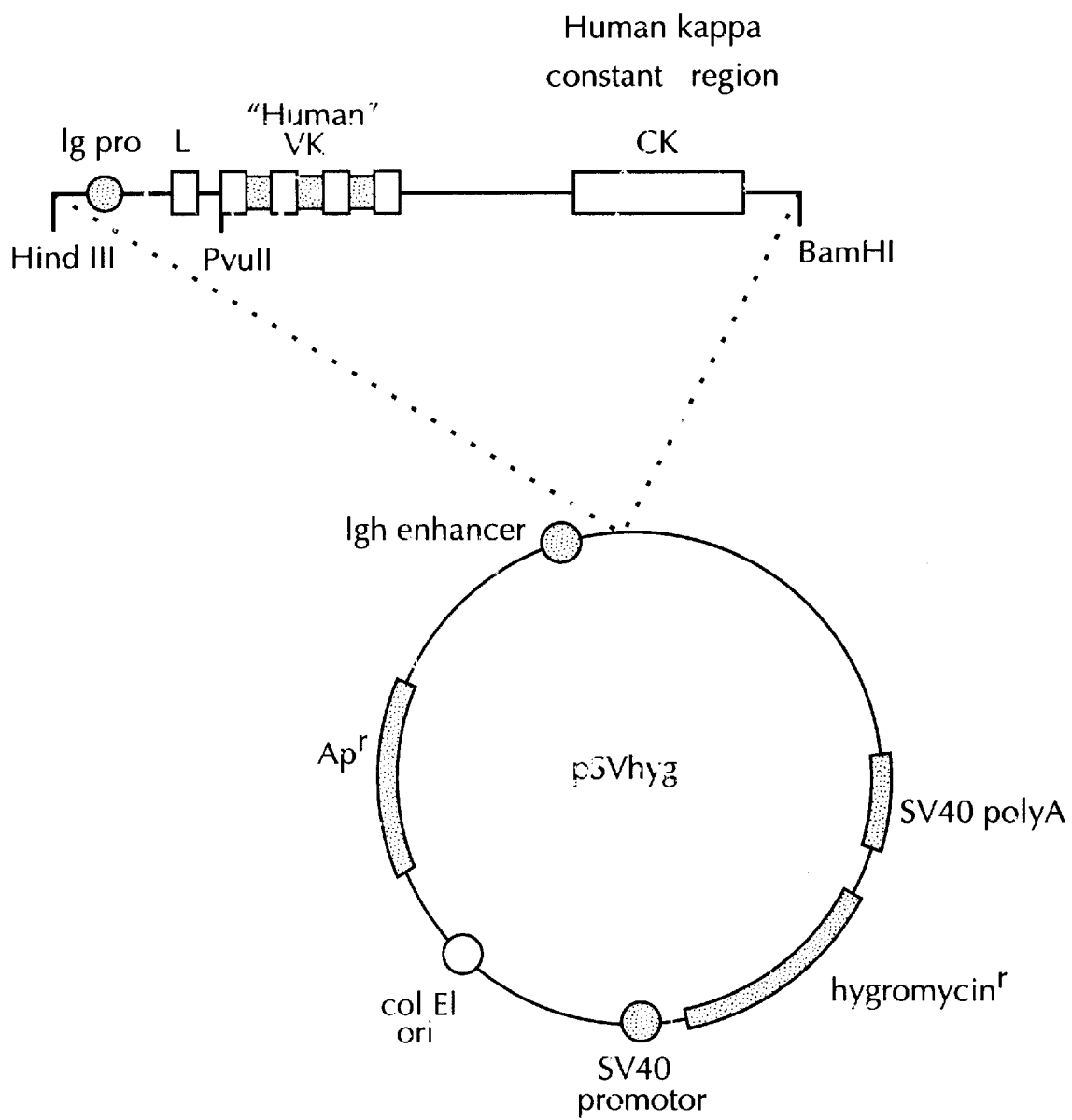
FIG. 4 Shows the vector pSVhyq for the expression of chimaeric or humanized light chains in mammalian cells.
Figure 5:
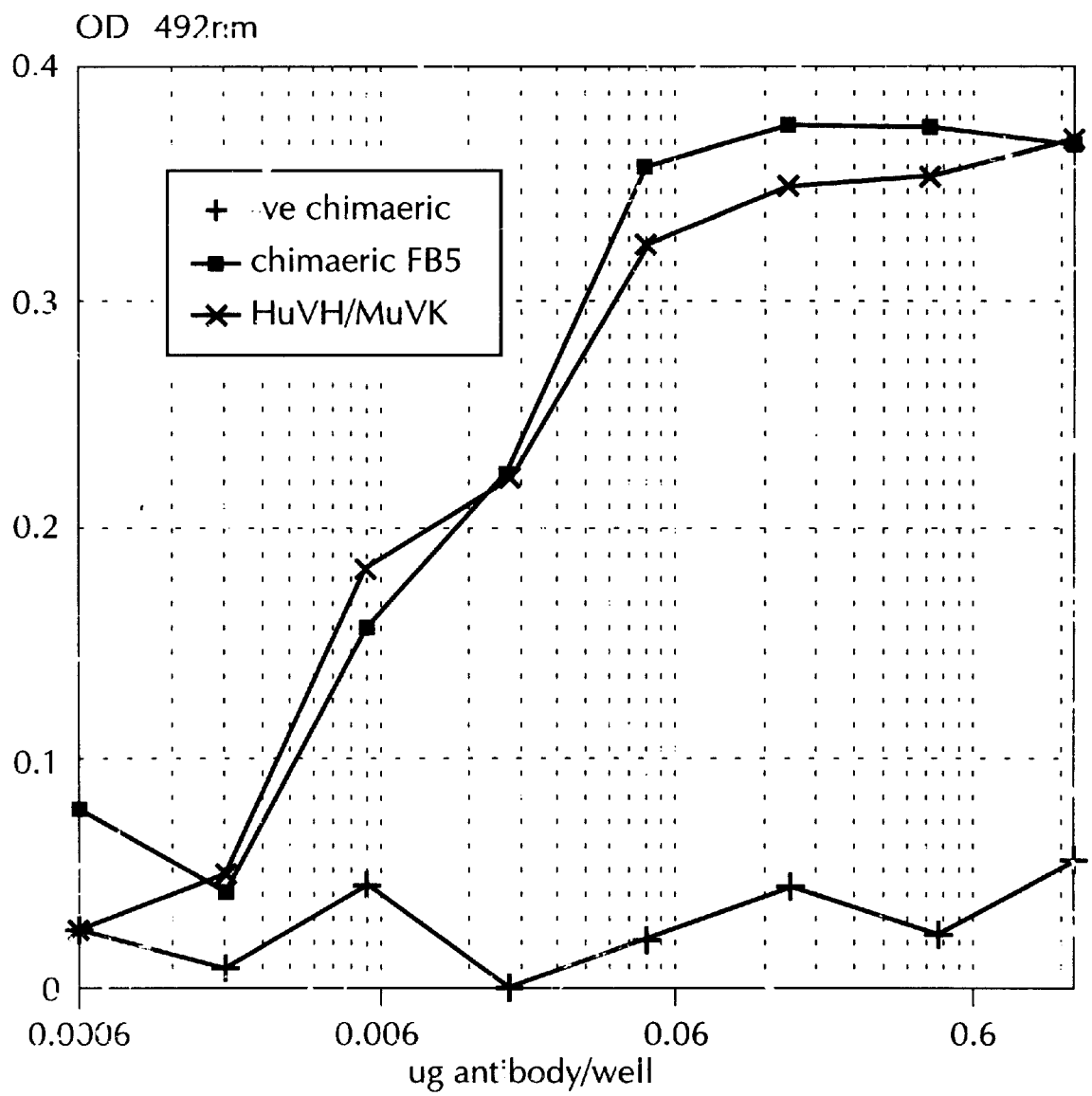
FIGS. 5–10 These figure provide graphical data of ELISA results demonstrating the binding properties of humanized FB5 specific antibodies.
Figure 6:
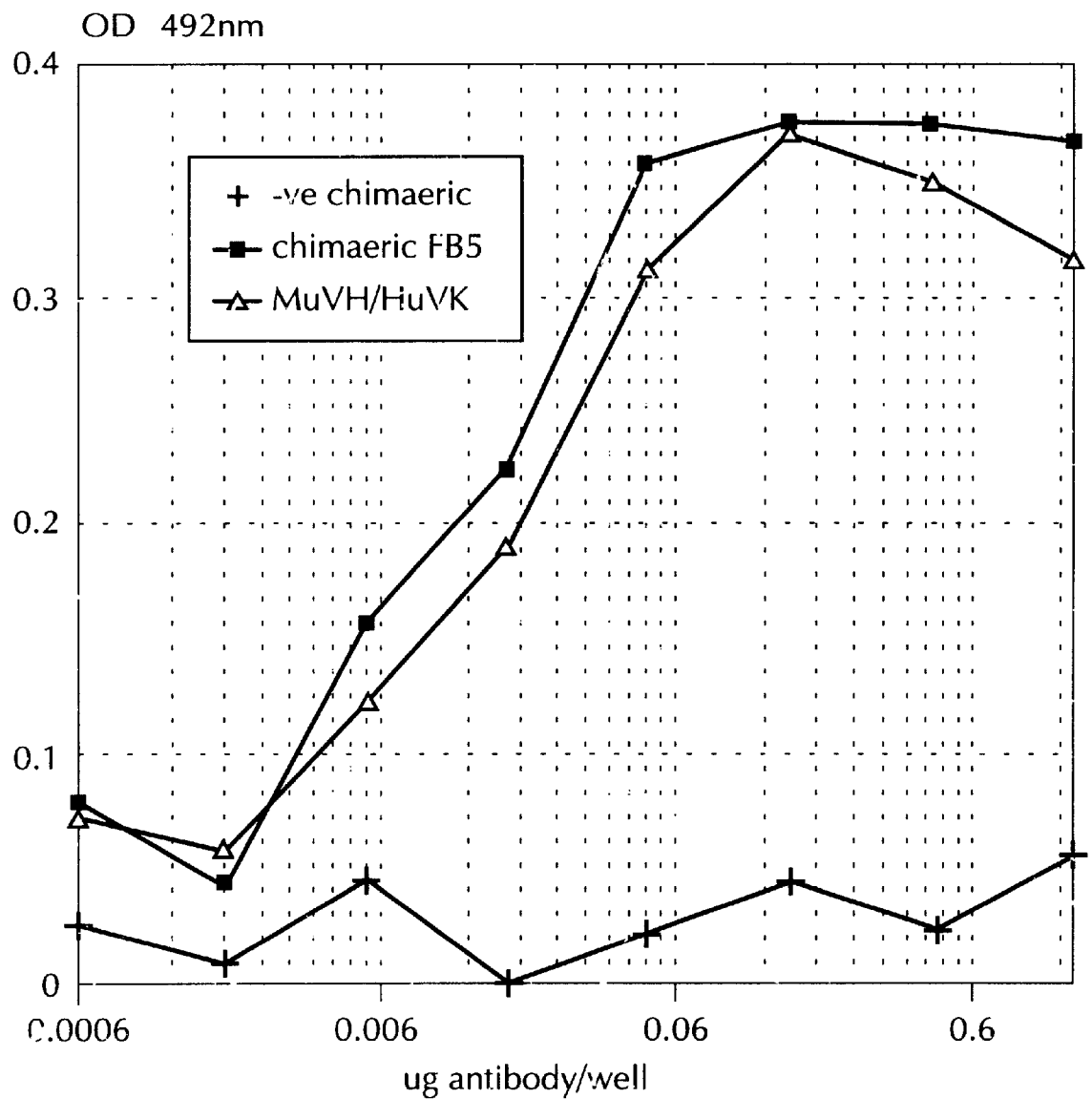
Figure 7:
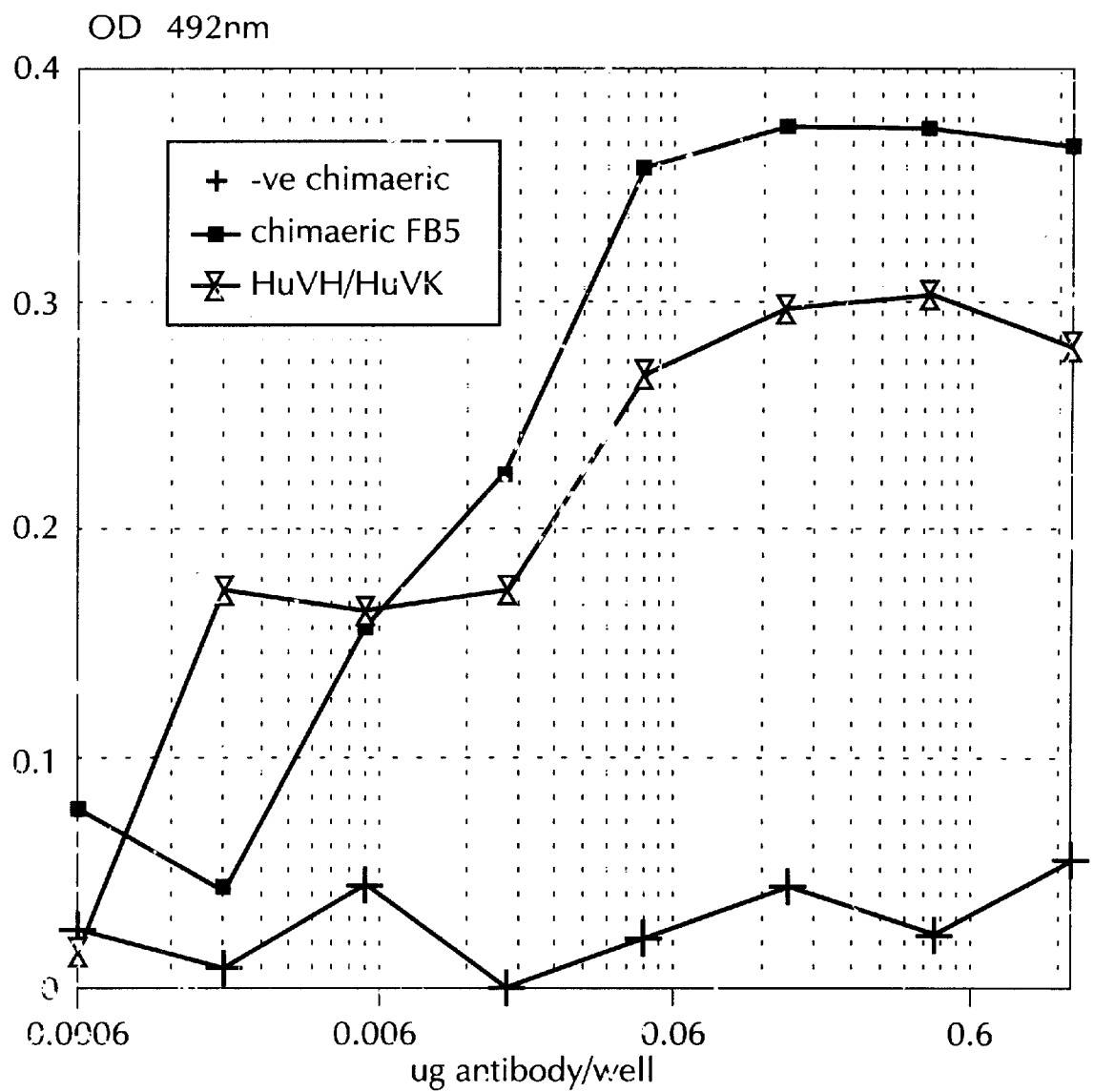
Figure 8:
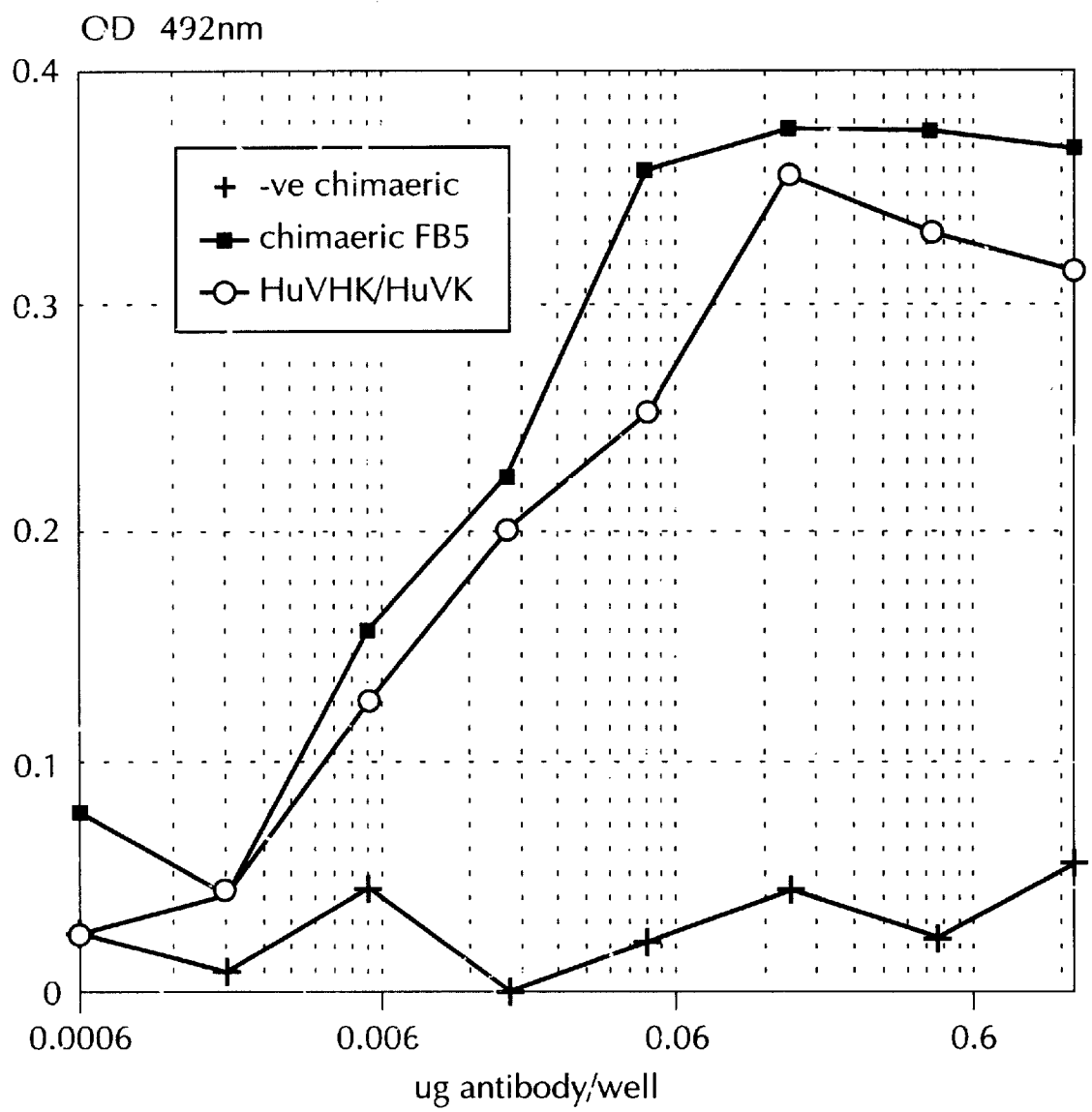
Figure 9:
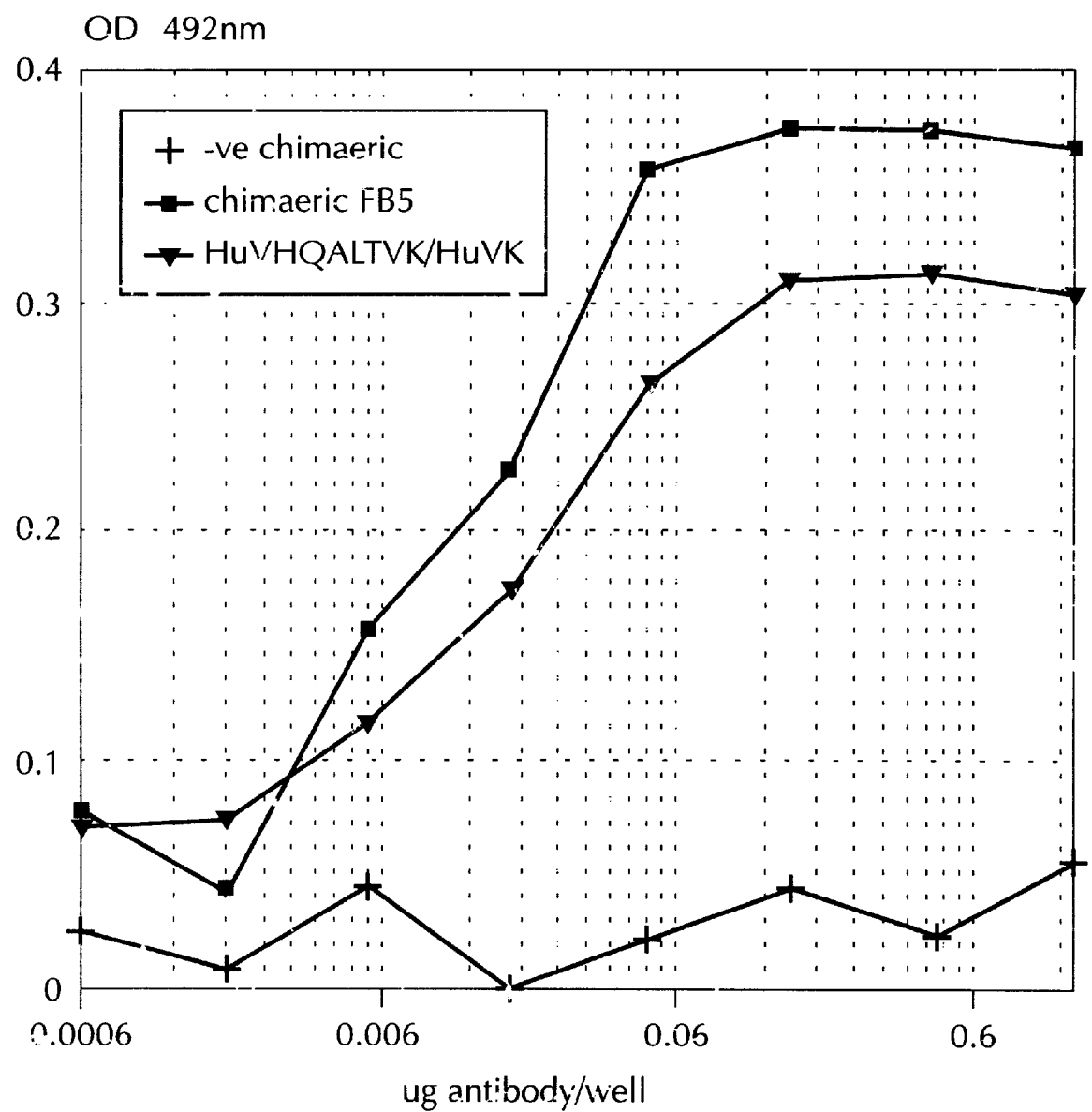
Figure 10:
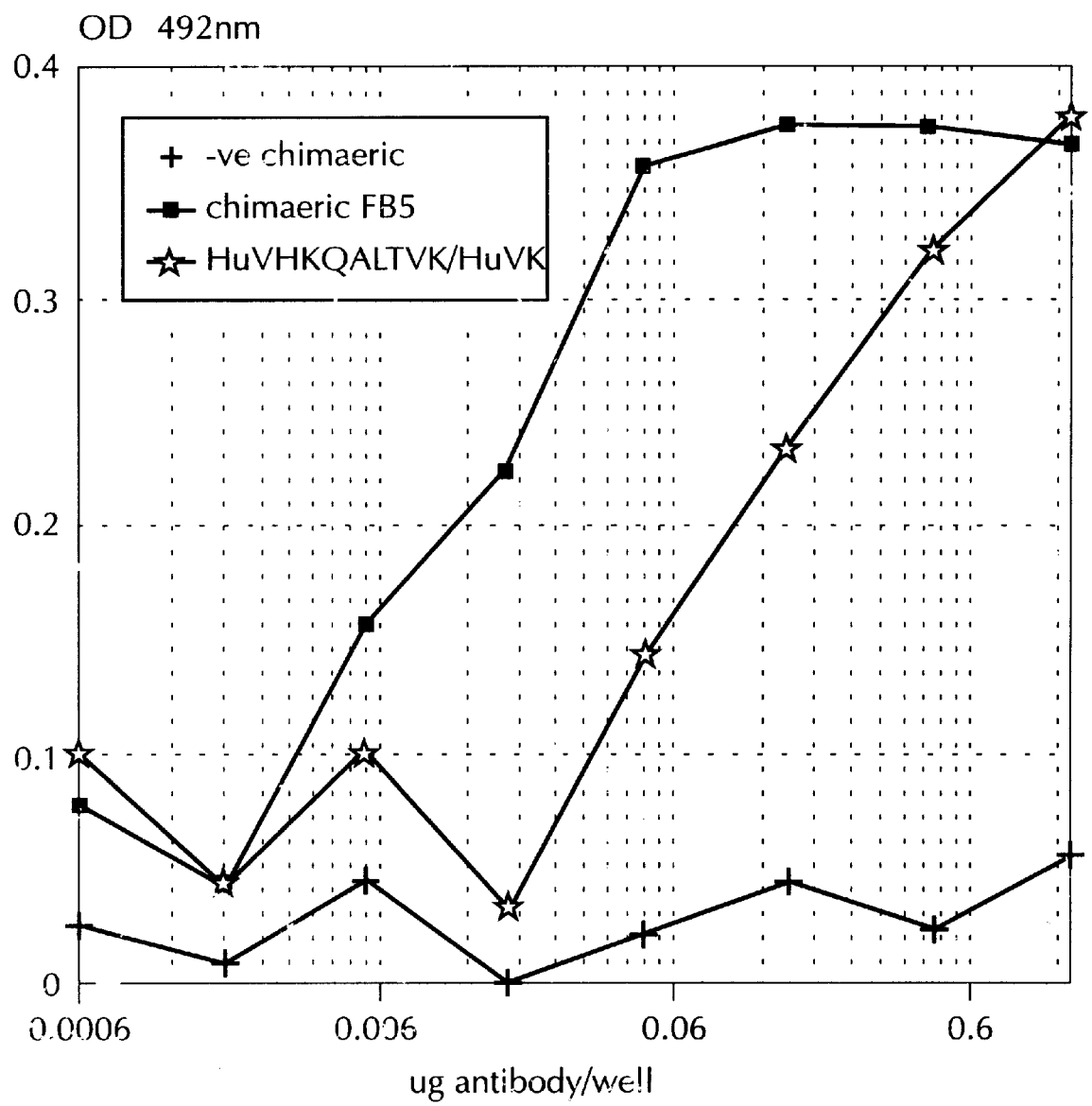

The expression vectors for the humanized VH and VK genes, pSVgpt and pSVhyg are shown in FIGS. 3 and 4. The humanized VH genes, together with the immunoglobulin heavy chain promoter, appropriate splice sites and signal peptide sequences were excised from the M13 clones with HindIII and BamHI and ligated into the heavy chain expression vector, pSVgpt. This vector contains the murine heavy chain immunoglobulin enhancer, the gpt gene under control of the SV40 promoter/enhancer for selection in mammalian cells, the human IgG1 constant region domain and sequences for replication and selection in *E. coli*. The humanized VK gene was cloned into the light chain expression vector pSVhyg in the same way. All features of pSVhyg are the same as in pSVgpt except that the got gene is replaced by the gene for hygromycin resistance (hyg) and a human kappa constant region is included instead of the IgG1 constant region.

For transfection into mammalian cells 10 µg of the heavy chain expression vector DNA and 20 µg of the light chain vector DNA were linearized by digestion with PvuI (Life Technologies Ltd, Paisley, U.K.), coprecipitated with ethanol and redissolved in 20 µl of water. The recipient cell line was NSO, a non-immunoglobulin producing mouse myeloma, obtained from the European collection of Animal Cell Cultures, Porton, U.K., ECAC No. 85110505 cells were grown in Dulbecco's Modified Eagle's Medium supplemented with 10% foetal calf serum and antibiotics (DMEM) (Life Technologies Ltd, Paisley, U.K.). Approximately $10^7$ NSO cells were harvested by centrifugation and resuspended in 0.5 ml DMEM, the digested DNA was added and the cells transferred to a cuvette and placed on ice for 5 min. A single pulse of 170 volts, 960µ farads was administered (Genepulser, BioRad, Richmond, Calif., U.S.A.). After a further 30 min on ice the cells were replaced in a flask in 20 ml DMEM and allowed to recover for 24 hours. After this time the cells were distributed into a 24 well plate in selective medium (DMEM with 0.8 µg/ml mycophenolic acid and 250 µg/ml xanthine). After 3 to 4 days the medium was changed for fresh selective medium. Colonies of transfected cells were visible after 10 to 14 days.

The production of human antibody in the wells containing transfected clones was measured by ELISA.

Capture antibody, goat anti-human IgG, gamma chain specific (Sera-Lab Ltd, Crawley Down, U.K.) was diluted to 5 µg/ml in 50 mM carbonate buffer pH9.6, and used to coat polystyrene ELISA plates (Dynatech Immulon 1), 200 µl per well, overnight at 4° C. After washing 3 times with PBST, 50–100 µl of the culture medium to be screened was added to the wells and incubated at 37° C. for 60 min. The wells were washed again with PBST and the reporter antibody, peroxidase-conjugated goat anti-human IgG, gamma chain specific (Sera-Lab Ltd, Crawley Down, U.K.) or peroxidase-conjugated goat anti-human kappa chain (Sera-Lab Ltd, Crawley Down, U.K) was added at 100 ng per well and the plate incubated for a further 60 min. The plate was washed as before then the colour was developed. Substrate buffer was prepared by mixing 100 mM citric acid and 100 mM disodium hydrogen phosphate to pH5.0. 25 mg of o-phenylenediamine was dissolved in 50 ml and 5 µl of 30% hydrogen peroxide added just before use. 200 µl was dispensed per well and incubated at room temperature in the dark. The reaction was stopped by addition of 50 µl per well of 12.5% sulphuric acid and the absorbances were read at 492 nm.

Positive cell clones were expanded for antibody purification. For the final expansion to production volume the cells were diluted in DMEM containing 10% IgG-free fetal calf serum. For small scale purification 500 ml of conditioned medium from static flask or spinner cultures was harvested by centrifugation and 0.1 volumes of 1.0M TrisHCl pH8.0 and 0.5 to 1.0 ml of Protein A-agarose (Boehringer Mannheim, Lewes, U.K.) were added. This was stirred overnight at room temperature then collected on a disposable column. This was washed with 10 column volumes of 0.1M TrisHCl pH8.0, 10 column volumes of 0.01M TrisHCl pH8.0 and eluted with 0.1M glycine buffer, pH3.0. 1.0 ml fractions were collected into tubes containing 100 µl of 1.0M TrisHCl, pH8.0. Fractions containing antibody were pooled and dialysed against PBS. The concentrations of the antibody preparations were determined using a Micro BCA Protein Assay Reagent Kit (Pierce, Rockford, USA). Samples were checked by running on 10% SDS-polyacrylamide gels.

Additional changs to the variable region were introduced in order to improve the affinity of the reshaped antibody, FB5HuVH/HuVK for FB5. The chimeric FB5 antibody, in which the murine constant region domains of the heavy and light chains had been replaced by the human constant regions used in the humanized antibody, was constructed as described by Orlandi et al., (1989). Two hybrid chimeric/humanized antibodies were constructed consisting of the chimeric heavy chain with the humanized light chain and the humanized heavy chain with the chimeric light chain. Both of these antibodies showed binding to the LA1-5s target cells with similar efficacies to the chimaeric and murine antibodies (within 3 fold). Despite these efficacies, further attention was directed towards the heavy and light chains in order to improve the affinity of the humanized antibody.

Three further versions of the FB5HuVH and the HUVK, were designed. The amino acid sequences of these VHs and VKs are shown in table 1.

Table 1 shows the variable region sequences of FB5HuVH, FB5HUVHK, FB5HuVHQA, LT, VK, FB5HuVHK,Q,A,LT,VK, FB5HuVK and FB5HuVKF. Murine framework residues are shown in lower case. Residue REI L(104) and T(107) are unusual residues for human subgroup I kappa chains; these residues have been replaced by the more common, V and K residues (underlined in table 1).

The additional changes to the HuVH and HuVK constructs are shown below (numbering according to Kabat et al., ibid):
FB5HuVHK (38), FB5HuVHQA,LT,VK (66–67, 69–70, 72–73),
FB5HuVHK,QA,LT,VK (38, 66–67 69–70, 72–73), and
FB5HuVKF (71). Two variations of the HuVKs shown in table 5 were constructed by inclusion of a Y residue at position 36.

These new versions were constructed by mutagenesis of the original reshaped heavy chain M13 single stranded DNA clone. The method of Higuchi, R. et al. (1988) Nucleic Acids Pes 16, 351–7367, which utilizes overlapping PCR amplification with mutagenic primers, was employed. The modified variable regions were cloned into the expression vector pSV pt as before and cotransfected with the MuVK plasmid into NSO cells. Antibody producing cell clones were selected, expanded and purified for testing. Subsequent to this, fully humanized version antibodies consisting of the modified HuVHs and HuVKs were prepared in the same way.

without fetal calf serum, serially diluted two fold. Incubation with test antibody was continued at room temperature for 1 hour after which cells were washed three times with PBSB and incubated with human red blood cells (type O+) conjugated to protein A (Pierce, Ill., USA) diluted in PBSB. Incubation with the indicator cells was continued at room temperature for 30 min after which unbound PA—RBCs were removed by washing twice with PBSB. The percentage resetting for each dilution of antibody was determined and the concentration of antibody required for 50% rosetting calculated. This data for the recombinant antibodies is presented below.

| Antibody | Concentration of antibody for 50% rosetting (ng/ml) |
|---|---|
| Murine FB5 | 3 |
| Chimaeric FB5 | 3 |
| FB5HuVH/HuVK | 80 |
| FB5HuVHK/HuVK | 16 |
| FB5HuVHK, QA, LT, VK/HuVK | 16 |

Appropriate negative controls were included in experiments

These and other recombinant antibodies have been tested in ELISAs using the LA1-5s target cells. The ELISA method used is as follows:

LA1-5s cells are diluted to $1.5 \times 10^5$–$2.5 \times 10^5$ cells/ml in DMEM, 10% FCS and 200 µl (ie $3$–$5 \times 10^4$ cells) added to each well. Cells are grown until nearly confluent (about 2 days). Plates are washed 2×with PBS and 100 µl antibody (diluted in DMEM) added. Incubation is carried out at 4° C.

TABLE 1

| | | |
|---|---|---|
| FB5HUVH: | QVQLQESGPGLVRPSQTLSLTCTaSGyTFtDYVI<br>HWVRQPPGRGLEWIGYINPYDDDTTYNQKFKGRV<br>TMLVDTSSNtaYLRLSSVTAeDTAVYYCARRGNS<br>YDGYFDYSMDYWGQGSLVTVSS | (SEQ ID NO:16) |
| FB5HuVHK: | QVQLQESGPGLVRPSQTLSLTCTaSGYTFtDYVX<br>HWVkQPPGRGLEWIGYINPYDDDTTYNQKFKGRV<br>TMLVDTSsNtayLRLSSVTAeDTAVYCARRGNS<br>YDGYFDYSMDYWGQGSLVTVSS | (SEQ ID NO:17) |
| FB5HuVHQA,LT,VK: | QVQLQESGPGLVRPSQTLSLTCTaSGyTFtDYV<br>WVRQPPcRGLEwIGYINPYDDDTTYNQKFKGqa<br>TltVVkSSNtaYLRLSSVTAeDTAVYYCARRGNS<br>YDGYFDYSMDYWGQGSLVTVSS | (SEQ ID NO:18) |
| FB5HuVHK,QA,LT,VK: | QVQLQESGPGLVRPSQTLSLTCTa6GyTFtDYVI<br>HWVkQPPGRGLEWIGYINPYDDDTTYNQKFKGga<br>TitVVkSSNtaYLRLSSVTAeDTAVYYCARRGNS<br>YDGYFDYSMOYWGQGSLVTVSS | (SEQ ID NO:19) |
| FB5HuVK: | DIQMTQSPSSLSASVGDRVTITCRASQNVGTAVA<br>WLQQTPGKAPKLLIYSASNRYTGVPSRFSGSGSG<br>TDYTFTYSSLQPEDIATYYCQQYTNYPMYTFGQG<br>TKVQIK | (SEQ ID NO:20) |
| FB5HuVKF: | DIQMTQSPSSLSASVGDRVTITCPASQNVGTAVA<br>WLQQTPGKAPKLLIYSASNRYTGVpSRFSGSGSG<br>TDFTFTISSLQPEDIATYYCQQYTNYPMYTFGQG<br>TKVQIK | (SEQ ID NO:21) |

Example 2
Specific Binding of Humanized FB5 Antibodies to Carcinoma Cells

Recombinant antibodies (chimaeric and humanized) were tested in mixed hemadsorption (MHA) resetting assays (Rettig et al. (1987) J. Immunol. 138, 4484–4489; Rettig et al. (1985) Cancer Res. 45, 815–821) for their ability to bind to LA1-5s target cells (human neuroblastoma cells). The cells were grown in 60 well Terasaki plates to form confluent monolayers. Cells were washed twice with PBSB and 10 µl of antibody added to the cells (antibodies diluted in DMEM for 1 hour. The wells are washed 3×with PBS and 100 µl of appropriate reporter antibody added, ie goat anti-human IgG1, HRPO conjugate (Sera-lab, 0.4 mg/ml, diluted in 1:500 in DMEM); incubation is carried out at 4° C. for 1 hour. Wells are washed 3×with PBS and bound reporter antibody detected using $H_2O_2$ and o-phenylenediaminedihydrochloride and the OD 492 nm measured.

The ELISA data presented in the attached graphs, together with the resetting data, indicate that humanized antibodies of the Examples bind the FB5 antigen. In particular the FB5HuVHK/HuVK antibody exhibits binding affinities close to the murine and chimaeric FB5 antibodies. Such recombinant antibodies (of which these are examples) therefore provide for novel, recombinant antibody molecules for the diagnosis and therapy of human cancers characterized by the expression of the FB5 antigen in the tumor stroma.

Incorporation by Reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

```
                          SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:1:

GGAAGCTTAG ACCGATGGGG CTGTTGTTTT G                                 31

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:2:

GGAAGCTTGA AGATGGATAC AGTTGGTGCA GC                                32

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

AGGTSMARCT GCAGSAGTCW GG                                           22

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

ACTAGTCGAC ATGGRCTTHM AGRTGSAG                                     28
```

(2) INFORMATION FOR SEQ ID NO:5:

(i) SEQUENCE CHARACTERISTICS:
    (A) LENGTH: 75 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:5:

```
CGTCCAGGTG GCTGTCTCAC CCAGTGTATA ACATAGTCAG TGAAGGTGTA G CCAGACGCG    60

GTGCAGGTCA GGCTC                                                     75
```

(2) INFORMATION FOR SEQ ID NO:6:

(i) SEQUENCE CHARACTERISTICS:
    (A) LENGTH: 76 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:6:

```
TTGTCACTCT GCCCTTGAAC TTCTGGTTGT AGGTAGTATC ATCATCATAA G GATTAATAT    60

ATCCAATCCA CTCAAG                                                    76
```

(2) INFORMATION FOR SEQ ID NO:7:

(i) SEQUENCE CHARACTERISTICS:
    (A) LENGTH: 96 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:7:

```
CCTGAGGAGA CGGTGACGAG ACTCCCTTGG CCCCAGTAGT CCATAGAGTA G TCAAAGTAA    60

CCATCATAGG AATTCCCCCT TCTTGCACAA TAATAG                              96
```

(2) INFORMATION FOR SEQ ID NO:8:

(i) SEQUENCE CHARACTERISTICS:
    (A) LENGTH: 69 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:8:

```
GGAGCCTTAC CTGGGGTCTG CTGGTACCAG GCTACAGCAG TACCCACATT C TGGCTGGCT    60

CTACAGGTG                                                            69
```

(2) INFORMATION FOR SEQ ID NO:9:

(i) SEQUENCE CHARACTERISTICS:
    (A) LENGTH: 48 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:9:

CTGCTTGGCA CACCAGTGTA CCGATTCGAT GCCGAGTAGA TCAGCAGC             48

(2) INFORMATION FOR SEQ ID NO:10:

(i) SEQUENCE CHARACTERISTICS:
        (A) LENGTH: 83 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:10:

CTACTCACGT TTGATTTGCA CCTTGGTCCC TTGGCCGAAC GTGTACATGG G ATAGTTGGT    60

ATATTGCTGG CAGTAGTAGG TGG                                            83

(2) INFORMATION FOR SEQ ID NO:11:

(i) SEQUENCE CHARACTERISTICS:
        (A) LENGTH: 64 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:11:

CGCGGTGTCC TCGGCTGTCA CGCTGCTGAG TCTCAGGTAG GCTGTGTTGG A GCTGGTGTC    60

TACC                                                                 64

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:12:

AACAGCTATG ACCATG                                                    16

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:13:

CTCTCTCAGG GCCAGGCGGT GA                                             22

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: DNA (genomic)

-continued (xi) SEQUENCE DESCRIPTION: SEQ ID NO:14:

GTAAAACGAC GGCCAGT                                                   17

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:15:

GCGGGCCTCT TCGCTATTAC GC                                             22

(2) INFORMATION FOR SEQ ID NO:16:

(i) SEQUENCE CHARACTERISTICS:
        (A) LENGTH: 124 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:16:

Gln Val Gln Leu Gln Glu Ser Gly Pro Gly Leu Val Arg Pro Ser Gln
1               5                   10                  15

Thr Leu Ser Leu Thr Cys Thr Ala Ser Gly Tyr Thr Phe Thr Asp Tyr
            20                  25                  30

Val Ile His Trp Val Arg Gln Pro Pro Gly Arg Gly Leu Glu Trp Ile
        35                  40                  45

Gly Tyr Ile Asn Pro Tyr Asp Asp Thr Thr Tyr Asn Gln Lys Phe
    50                  55                  60

Lys Gly Arg Val Thr Met Leu Val Asp Thr Ser Ser Asn Thr Ala Tyr
65                  70                  75                  80

Leu Arg Leu Ser Ser Val Thr Ala Glu Asp Thr Ala Val Tyr Tyr Cys
            85                  90                  95

Ala Arg Arg Gly Asn Ser Tyr Asp Gly Tyr Phe Asp Tyr Ser Met Asp
            100                 105                 110

Tyr Trp Gly Gln Gly Ser Leu Val Thr Val Ser Ser
            115                 120

(2) INFORMATION FOR SEQ ID NO:17:

(i) SEQUENCE CHARACTERISTICS:
        (A) LENGTH: 124 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:17:

Gln Val Gln Leu Gln Glu Ser Gly Pro Gly Leu Val Arg Pro Ser Gln
1               5                   10                  15

Thr Leu Ser Leu Thr Cys Thr Ala Ser Gly Tyr Thr Phe Thr Asp Tyr
            20                  25                  30

Val Ile His Trp Val Lys Gln Pro Pro Gly Arg Gly Leu Glu Trp Ile
        35                  40                  45

```
Gly Tyr Ile Asn Pro Tyr Asp Asp Asp Thr Thr Tyr Asn Gln Lys Phe
 50                  55                  60

Lys Gly Arg Val Thr Met Leu Val Asp Thr Ser Ser Asn Thr Ala Tyr
 65                  70                  75                  80

Leu Arg Leu Ser Ser Val Thr Ala Glu Asp Thr Ala Val Tyr Tyr Cys
                 85                  90                  95

Ala Arg Arg Gly Asn Ser Tyr Asp Gly Tyr Phe Asp Tyr Ser Met Asp
            100                 105                 110

Tyr Trp Gly Gln Gly Ser Leu Val Thr Val Ser Ser
            115                 120
```

(2) INFORMATION FOR SEQ ID NO:18:

(i) SEQUENCE CHARACTERISTICS:
        (A) LENGTH: 124 amino acids
        (B) TYPE: amino acid
        (C) STRANDEDNESS: unknown
        (D) TOPOLOGY: unknown (ii) MOLECULE TYPE:

(xi) SEQUENCE DESCRIPTION: SEQ ID NO:18:

```
Gln Val Gln Leu Gln Glu Ser Gly Pro Gly Leu Val Arg Pro Ser Gln
 1               5                  10                  15

Thr Leu Ser Leu Thr Cys Thr Ala Ser Gly Tyr Thr Phe Thr Asp Tyr
                 20                  25                  30

Val Ile His Trp Val Arg Gln Pro Pro Gly Arg Gly Leu Glu Trp Ile
             35                  40                  45

Gly Tyr Ile Asn Pro Tyr Asp Asp Asp Thr Thr Tyr Asn Gln Lys Phe
 50                  55                  60

Lys Gly Gln Ala Thr Leu Thr Val Val Lys Ser Ser Asn Thr Ala Tyr
 65                  70                  75                  80

Leu Arg Leu Ser Ser Val Thr Ala Glu Asp Thr Ala Val Tyr Tyr Cys
                 85                  90                  95

Ala Arg Arg Gly Asn Ser Tyr Asp Gly Tyr Phe Asp Tyr Ser Met Asp
            100                 105                 110

Tyr Trp Gly Gln Gly Ser Leu Val Thr Val Ser Ser
            115                 120
```

(2) INFORMATION FOR SEQ ID NO:19:

(i) SEQUENCE CHARACTERISTICS:
        (A) LENGTH: 124 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:19:

```
Gln Val Gln Leu Gln Glu Ser Gly Pro Gly Leu Val Arg Pro Ser Gln
 1               5                  10                  15

Thr Leu Ser Leu Thr Cys Thr Ala Ser Gly Tyr Thr Phe Thr Asp Tyr
                 20                  25                  30

Val Ile His Trp Val Lys Gln Pro Pro Gly Arg Gly Leu Glu Trp Ile
             35                  40                  45

Gly Tyr Ile Asn Pro Tyr Asp Asp Asp Thr Thr Tyr Asn Gln Lys Phe
 50                  55                  60

Lys Gly Gln Ala Thr Leu Thr Val Val Lys Ser Ser Asn Thr Ala Tyr
 65                  70                  75                  80
```

Leu Arg Leu Ser Ser Val Thr Ala Glu Asp Thr Ala Val Tyr Tyr Cys
                85                  90                  95

Ala Arg Arg Gly Asn Ser Tyr Asp Gly Tyr Phe Asp Tyr Ser Met Asp
                100                 105                 110

Tyr Trp Gly Gln Gly Ser Leu Val Thr Val Ser Ser
                115                 120

(2) INFORMATION FOR SEQ ID NO:20:

(i) SEQUENCE CHARACTERISTICS:
        (A) LENGTH: 108 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:20:

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Ala
                20                  25                  30

Val Ala Trp Leu Gln Gln Thr Pro Gly Lys Ala Pro Lys Leu Leu Ile
            35                  40                  45

Tyr Ser Ala Ser Asn Arg Tyr Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Thr Asn Tyr Pro Met
                85                  90                  95

Tyr Thr Phe Gly Gln Gly Thr Lys Val Gln Ile Lys
                100                 105

(2) INFORMATION FOR SEQ ID NO:21:

(i) SEQUENCE CHARACTERISTICS:
        (A) LENGTH: 108 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:21:

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Ala
                20                  25                  30

Val Ala Trp Leu Gln Gln Thr Pro Gly Lys Ala Pro Lys Leu Leu Ile
            35                  40                  45

Tyr Ser Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Thr Asn Tyr Pro Met
                85                  90                  95

Tyr Thr Phe Gly Gln Gly Thr Lys Val Gln Ile Lys
                100                 105

(2) INFORMATION FOR SEQ ID NO:22:

(i) SEQUENCE CHARACTERISTICS:
        (A) LENGTH: 372 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:22:

```
CAGGTSMARC TGCAGSAGTC WGGACCTGAG CTGGTGAAGC CTGGGGCTTC A GTGAAGATG      60

TCCTGCAAGG CTTCTGGATA CACATTCACT GACTATGTTA TACACTGGAT G AAGCAGAGA     120

AATGGAAAGA GCCTTGAGTG GATTGGATAT ATTAATCCTT ATGATGATGA T ACTACCTAC     180

AACCAGAAGT TCAAGGGCCA GGCCACATTG ACTGTAGTCA AATCCTCCAA C ACAGCCTAC     240

ATGCAGCTCA ACAGCCTGAC ATCTGAGGAC TCTGCAGTCT ATTACTGTGC A AGAAGGGGG     300

AATTCCTATG ATGGTTACTT CGACTATTCT ATGGACTACT GGGGTCAAGG A ACCTCAGTC     360

ACCGTCTCCT CA                                                          372
```

(2) INFORMATION FOR SEQ ID NO:23:

(i) SEQUENCE CHARACTERISTICS:
        (A) LENGTH: 124 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: Xaa
        (B) LOCATION: 3..4
        (D) OTHER INFORMATION: Xaa = Lys or Glu (ix) FEATURE:
        (A) NAME/KEY: Xaa
        (B) LOCATION: 6..7
        (D) OTHER INFORMATION: Xaa = Glu or Gln (xi) SEQUENCE DESCRIPTION: SEQ ID NO:23:

```
Gln Val Xaa Leu Gln Xaa Ser Gly Pro Glu L eu Val Lys Pro Gly Ala
1               5                   10                  15

Ser Val Lys Met Ser Cys Lys Ala Ser Gly T yr Thr Phe Thr Asp Tyr
            20                  25                  30

Val Ile His Trp Met Lys Gln Arg Asn Gly L ys Ser Leu Glu Trp Ile
        35                  40                  45

Gly Tyr Ile Asn Pro Tyr Asp Asp Asp Thr T hr Tyr Asn Gln Lys Phe
    50                  55                  60

Lys Gly Gln Ala Thr Leu Thr Val Val Lys S er Ser Asn Thr Ala Tyr
65                  70                  75                  80

Met Gln Leu Asn Ser Leu Thr Ser Glu Asp S er Ala Val Tyr Tyr Cys
                85                  90                  95

Ala Arg Arg Gly Asn Ser Tyr Asp Gly Tyr P he Asp Tyr Ser Met Asp
            100                 105                 110

Tyr Trp Gly Gln Gly Thr Ser Val Thr Val S er Ser
        115                 120
```

(2) INFORMATION FOR SEQ ID NO:24:

(i) SEQUENCE CHARACTERISTICS:
        (A) LENGTH: 325 base pairs
        (B) TYPE: nucleic acid -continued

```
    (C) STRANDEDNESS: unknown
    (D) TOPOLOGY: unknown (ii) MOLECULE TYPE: DNA (genomic)

(xi) SEQUENCE DESCRIPTION: SEQ ID NO:24:

GACATTGTGA TGACCCAGTC TCAAAAATTC ATGTCCACAT CAGTAGGAGA C CAGGGTCAA      60

CATCACCTGC AGGGCCAGTC AGAATGTGGG TACTGCTGTA GCCTGGTATC A ACAGAAACC     120

AGGACAATCT CCTAAATTAC TGATTTACTC GGCATCGAAT CGGTACACTG G AGTCCCTGA    180

TCGCTTCACA GGCAGTGGAT CTGGGACAGA TTTCACTCTC ACCATCAGCA A TATGCAGTC    240

TGAAGACCTG GCAGATTATT TCTGCCAGCA ATATACCAAC TATCCCATGT A CACGTTTGG    300

AGGGGGGACC AAGCTGGAAA TAAAA                                            325

(2) INFORMATION FOR SEQ ID NO:25:

(i) SEQUENCE CHARACTERISTICS:
        (A) LENGTH: 108 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:25:

Asp Ile Val Met Thr Gln Ser Gln Lys Phe M et Ser Thr Ser Val Gly
1               5                   10                  15

Asp Arg Val Asn Ile Thr Cys Thr Ala Ser G ln Asn Val Gly Thr Ala
                20                  25                  30

Val Ala Trp Tyr Gln Gln Lys Pro Gly Gln S er Pro Lys Leu Leu Ile
            35                  40                  45

Tyr Ser Ala Ser Asn Arg Tyr Thr Gly Val P ro Asp Arg Phe Thr Gly
        50                  55                  60

Ser Gly Ser Gly Thr Asp Phe Thr Leu Thr I le Ser Asn Met Gln Ser
65                  70                  75                  80

Glu Asp Leu Ala Asp Tyr Phe Cys Gln Gln T yr Thr Asn Tyr Pro Met
                85                  90                  95

Tyr Thr Phe Gly Gly Gly Thr Lys Leu Glu I le Lys
                100                 105
```

What is claimed is:

1. A method for treating a subject with cancer, cells of which present antigen FB5 on their surfaces comprising administering to said subject a therapeutically effective amount of a conjugate of a humanized antibody which specifically bins to an FB5 antigen, comprising a humanized variable region having a heavy chain region and a light chain region, said heavy chain region having an amino acid sequence selected from the group consisting of SEQ ID NOS: 16, 17, 18, and 19, and said light chain region having an amino acid sequence selected from the group consisting of SEQ ID NOS: 20 and 21, and a label having a therapeutic property.

2. The method of claim 1, wherein said subject is a human.

3. The method according to claim 1 wherein the heavy chain region has the amino acid sequence of SEQ ID NO: 16 and the light chain region has the amino acid sequence of SEQ ID NO: 20.

4. The method according to claim 1 wherein the heavy chain region has the amino acid sequence of SEQ ID NO: 17 and the light chain region has the amino acid sequence of SEQ ID NO: 20.

5. The method according to claim 1 wherein the heavy chain region has the amino acid sequence of SEQ ID NO: 18 and the light chain region has the amino acid sequence of SEQ ID NO: 20.

6. The method according to claim 1 wherein the heavy chain region has the amino acid sequence of SEQ ID NO: 19 and the light chain region has the amino acid sequence of SEQ ID NO: 20.

7. The method according to claim 1, wherein the heavy chain region has the amino acid sequence of SEQ ID NO: 16 and the light chain region has the amino acid sequence of SEQ ID NO: 21.

8. The method according to claim 1 wherein the heavy chain region has the amino acid sequence of SEQ ID NO: 17 and the light chain region has the amino acid sequence of SEQ ID NO: 21.

9. The method according to claim 1 wherein the heavy chain region has the amino acid sequence of SEQ ID NO: 18 and the light chain region has the amino acid sequence of SEQ ID NO: 21.

10. The method according to claim 1 wherein the heavy chain region has the amino acid sequence of SEQ ID NO: 21.

11. The method of claim 1 wherein said label is a radionuclide.

12. The method of claim 11 wherein said radionuclide is $^{125}$I, $^{131}$I, or $^{14}$C.

13. The method of claim 1, wherein said antigen FB5 is present on the luminal surface of tumor vascular cells.

14. The method of claim 1, wherein said cancer cells are cells of a cancer selected from the group consisting of carcinoma, neuroectodermal cancer, and sarcoma.

* * * * *